US009562080B2

United States Patent

Urbanowicz et al.

(10) Patent No.: US 9,562,080 B2
(45) Date of Patent: Feb. 7, 2017

(54) LYME DISEASE VACCINE, GENETIC CONSTRUCT, RECOMBINANT PROTEIN, METHOD FOR DESIGNING GENETIC CONSTRUCT, METHOD FOR PRODUCING VACCINE, METHOD FOR PRODUCING RECOMBINANT PROTEINS, USE OF RECOMBINANT PROTEINS IN THE PRODUCTION OF LYME DISEASE VACCINE

(71) Applicant: INSTYTUT CHEMII BIOORGANICZNEJ PAN, Poznań (PL)

(72) Inventors: Anna Urbanowicz, Poznań (PL); Marek Figlerowicz, Poznań (PL); Dominik Lewandowski, Poznań (PL)

(73) Assignee: INSTYTUT CHEMII BIOORGANICZNEJ PAN, Poznan (PL)

(*) Notice: Subject to any disclaimer, the term of this patent is extended or adjusted under 35 U.S.C. 154(b) by 0 days.

(21) Appl. No.: 14/385,500

(22) PCT Filed: Oct. 21, 2013

(86) PCT No.: PCT/PL2013/000133
§ 371 (c)(1),
(2) Date: Sep. 16, 2014

(87) PCT Pub. No.: WO2014/065679
PCT Pub. Date: May 1, 2014

(65) Prior Publication Data

US 2015/0093408 A1 Apr. 2, 2015

(30) Foreign Application Priority Data

Oct. 22, 2012 (PL) ........................................ 401324

(51) Int. Cl.

| | |
|---|---|
| ***A61K 39/00*** | (2006.01) |
| ***A61K 47/00*** | (2006.01) |
| ***A61K 45/00*** | (2006.01) |
| ***C12N 15/00*** | (2006.01) |
| ***C12N 15/09*** | (2006.01) |
| ***C12N 15/64*** | (2006.01) |
| ***C07K 1/00*** | (2006.01) |
| ***C07K 14/00*** | (2006.01) |
| ***C07K 17/00*** | (2006.01) |
| ***C07K 14/435*** | (2006.01) |
| ***A61K 39/02*** | (2006.01) |
| ***A61K 45/06*** | (2006.01) |
| *A61K 38/00* | (2006.01) |
| *C12N 15/86* | (2006.01) |
| *A61K 39/39* | (2006.01) |
| *C07K 14/445* | (2006.01) |

(52) U.S. Cl.
CPC ..... *C07K 14/43527* (2013.01); *A61K 39/0003* (2013.01); *A61K 39/0225* (2013.01); *A61K 45/06* (2013.01); *C12N 15/64* (2013.01); *A61K 38/00* (2013.01); *A61K 39/00* (2013.01); *A61K 39/39* (2013.01); *C07K 14/445* (2013.01); *C12N 15/86* (2013.01)

(58) Field of Classification Search
CPC ........ A61K 39/00; A61K 39/39; A61K 38/00; C07K 14/445; C12N 15/86
See application file for complete search history.

(56) References Cited

U.S. PATENT DOCUMENTS 6,676,942 B1 1/2004 Lobet et al.

FOREIGN PATENT DOCUMENTS

| | | | |
|---|---|---|---|
| WO | 0216422 | A3 | 2/2002 |
| WO | 2006014292 | A2 | 2/2006 |

OTHER PUBLICATIONS

Pal et al., Cell, 2004; 119: 457-468.*
Mayo Clinic, http://www.mayoclinic.org/diseases-conditions/lyme-disease/basics/prevention/con-20019701, accessed on Mar. 23, 2016.*
Miller, L. A. et al., Oral Vaccination of White-Tailed Deer Using a Recombinant Bacillus Calmette-Guérin Vaccine Expressing the Borrelia burgdorferi Outer Surface Protein A: Prospects for Immunocontraception. American Journal of Reproductive Immunology, Apr. 1999, vol. 41, pp. 279-285, Ireland.
Dunne, M. et al., Oral vaccination with an attenuated *Salmonella typhimurium* strain expressing Borrelia burgdorferi OspA prevents murine Lyme borreliosis. Infection and Immunity, Apr. 1995, vol. 63 No. 4, pp. 1611-1614.

(Continued)

*Primary Examiner* — Gary Nickol
*Assistant Examiner* — Lakia Tongue
(74) *Attorney, Agent, or Firm* — Venjuris PC

(57) ABSTRACT

The present invention relates to a Lyme disease vaccine, a genetic construct, recombinant protein, method for genetic construct design, method for vaccine delivery, method for recombinant proteins delivery, use of recombinant proteins in the production of Lyme disease vaccine. In particular, the method concerns the use of TROSPA and TROSPA-Salp15 recombinant proteins derived from castor bean tick (*Ixodes riccinus*) as a component of Lyme disease vaccine for animals. The antibodies present in blood of an immunized vertebrate directed against the TROSPA proteins considerably reduce the chance of infecting new ticks by blocking or hindering the interaction of TROSPA protein with OspA protein of *Borrelia burgdorferi* sensu lato. The interaction is crucial in the process of the spirochete entering a tick. The antibodies directed against the TROSPA-Salp15 protein protect vertebrates from infection on the stage of *Borellia* diffusion by destroying their protective coating formed at the surface as a result of the interaction between the Salp15 tick protein and OspC spirochete protein. The vaccine based on TROSPA tick proteins and TROSPA-Salp15 proteins may be used independently or together with the OspA recombinant proteins and OspC protein of *Borrelia burgdorferi* sensu lato.

5 Claims, 11 Drawing Sheets

(56) References Cited

OTHER PUBLICATIONS

Figure 1:
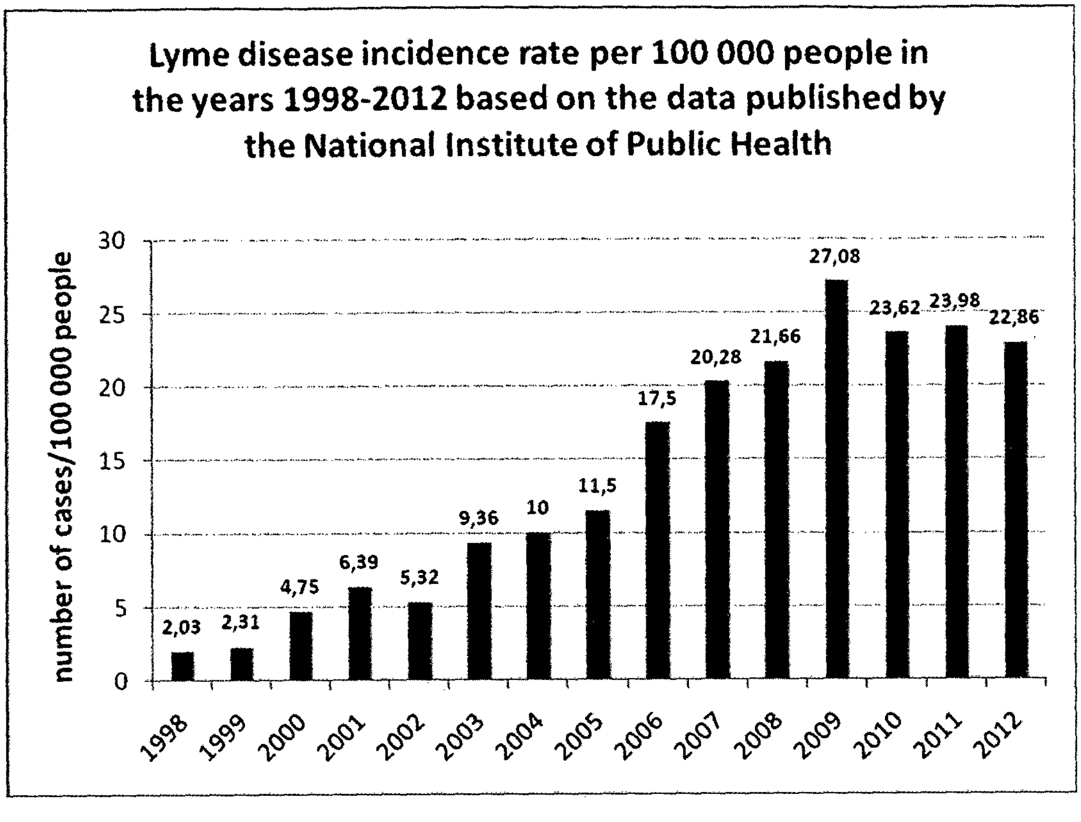

Joppe W.R. Hovius et al., Tick-host-pathogen interactions in Lyme borreliosis, Trends in Parasitology, Sep. 1, 2007, vol. 23, No. 9, pp. 434-438.
Pal, Utpal et al., TROSPA, an Ixodes scapularis receptor for Borrelia burgdorferi, CELL, Nov. 12, 2004, vol. 119, No. 4, pp. 457-468.
Jianfeng Dai et al., Antibodies against a tick protein, Salp15, protect mice from the Lyme disease agent, Cell Host Microbe, Nov. 19, 2009, vol. 6, No. 5, pp. 482-492.
Juan Anguita et al., Salp15, an Ixodes scapularis Salivary Protein, Inhibits CD4+ T Cell Activation, Immunity, Jun. 1, 2002, vol. 16, No. 6, pp. 849-859.
Marek Figlerowicz et al., Functional Insights into Recombinant TROSPA Protein from Ixodes ricinus, PLOS One, Oct. 18, 2013, vol. 8, No. 10, pp. 1-10.
Satoru Konnai et al., Identification of TROSPA homologue in Ixodes persulcatus Schulze, the specific vector for human Lyme borreliosis in Japan, Ticks and Tick-Bone Diseases, Apr. 1, 2012, vol. 3, No. 2, pp. 75-77.
Pal, Utpal et al., Supplemental Data: TROSPA, an Ixodes scapularis receptor for Borrelia burgdorferi, CELL, Nov. 12, 2004, vol. 119, No. 4, pp. S1-S5+1.

* cited by examiner

Fig. 2A

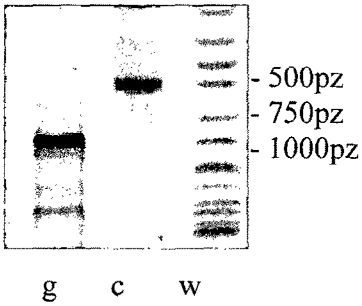

Fig. 2B

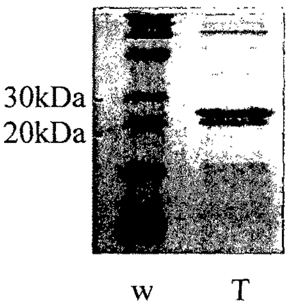

Fig. 2C

```
gb|EU034646   ---------- ---------- ---------- ---------- ---------- ----------
TROSPA        ATGCGGGGTT CTCATCATCA TCATCATCAT GGTATGGCTA GCATGACTGG TGGACAGCAA

gb|EU034646   ---------- ---------- ---------- ---------- --------AT GGCGGCTATG
TROSPA        ATGGGTCGGG ATCTGTACGA CGATGACGAT AAGGATCATC CCTTCACCAT GGCGGCTATG
                                                                  ** **********

gb|EU034646   GAGGCTATGG CGGTGGATAT GGAGGCTATG GCGGCGGCTA TGGCGGCGGC TATGGTGGCT
TROSPA        GAGGCTATGG CGGTGGATAT GGAGGCTATG GCGGCGGCTA TGGCGGCGGC TATGGTGGCT
              ********** ********** ********** ********** ********** **********

gb|EU034646   ACGGACACGG TGGCTTCCTC GGCGGCTTCG GCTATGGCCA CGGAGGCTAC GGTGGCTATG
TROSPA        ACGGACACGG TGGCTTCCTC GGCGGCTTCG GCTATGGCCA CGGAGGCTAC GGTGGCTATG
              ********** ********** ********** ********** ********** **********

gb|EU034646   GACACGGCGT CGCTGTCGCT GCCGCTCCAG TTGTCGCCAA GGTCGCTGCC CCAGTCGTCG
TROSPA        GACACGGCGT CGCTGTCGCT GCCGCTCCAG TTGTCGCCAA GGTCGCTGCC CCAGTCGTCG
              ********** ********** ********** ********** ********** **********

gb|EU034646   CTGTCGGCCA CGGCGGCTAC GGTGGCTACG GACACGGTGG TTTCCTCGGC GGATACGGAG
TROSPA        CTGTCGGCCA CGGCGGCCAC GGTGGCTACG GACACGGTGG TTTCCTCGGC GGATACGGAG
              ********** *******  ** ********** ********** ********** **********

gb|EU034646   GTTACGGACA CGGAGGATTC GGCGGCTACG GTCTCGGCCA CGGCGTCGCT GTCCATGCTG
TROSPA        GTTACGGACA CGGAGGATTC GGCGGCTACG GTCTCGGCCA CGGCGTCGCT GTCCATGCTG
              ********** ********** ********** ********** ********** **********

gb|EU034646   CCCCAGTTGT CGCCAAGGTC GCTGCCCCAG TCGTCGCTGT CGGCCACGGC TACGGAGGCT
TROSPA        CCCCAGTTGT CGCCAAGGTC GCTGCCCCAG TCGTCGCTGT CGGCCACGGC TACGGAGGCT
              ********** ********** ********** ********** ********** **********

gb|EU034646   TCGGTTACGG CGGATATGGC GGACACGGCT ACGGACACTA AGCAATTCAT CTCAAAGGGA
TROSPA        TCGGTTACAG CGGATATGGC GGACACGGCT ACGGACACTA AGCAATTCAT CTCAAAGGGA
              ********.* ********** ********** ********** ********** **********

gb|EU034646   AACCAACACT TCTTCGCCGC TTCTTATTTA TGCGCTTGGG CCGACCAGAG CGCCGCTGGA
TROSPA        AACCAACACT TCTTCGCCGC TTCTTATTTA TGCGCTTGGG CCGACCAGAG CGCCGCTGGA
              ********** ********** ********** ********** ********** **********

gb|EU034646   AGTTGA
TROSPA        AGTTGA
              ******
```

Fig. 2

```
TROSPA-Salp15      ATGCGGGGTTCTCATCATCATCATCATCATGGTATGGCTAGCATGACTGGTGGACAGCAA
gb|EU128526.1|     ------------------------------------------------------------
gb|EU034646.1|     ------------------------------------------------------------

TROSPA-Salp15      ATGGGTCGGGATCTGTACGACGATGACGATAAGGATCATCCCTTCACCAATGGCGGCTAT
gb|EU128526.1|     ------------------------------------------------------------
gb|EU034646.1|     -------------------------------------------------ATGGCGGCTAT
                                                                    ***********

TROSPA-Salp15      GGAGGCTATGGCGGTGGATATGGAGGCTATGGCGGCGGCTATGGCGGCGGCTATGGTGGC
gb|EU128526.1|     ------------------------------------------------------------
gb|EU034646.1|     GGAGGCTATGGCGGTGGATATGGAGGCTATGGCGGCGGCTATGGCGGCGGCTATGGTGGC
                   ************************************************************

TROSPA-Salp15      TACGGACACGGTGGCTTCCTCGGCGGCTTCGGCTATGGCCACGGAGGCTACGGTGGCTAT
gb|EU128526.1|     ------------------------------------------------------------
gb|EU034646.1|     TACGGACACGGTGGCTTCCTCGGCGGCTTCGGCTATGGCCACGGAGGCTACGGTGGCTAT
                   ************************************************************

TROSPA-Salp15      GGACACGGCGTCGCTGTCGCTGCCGCTCCAGTTGTCGCCAAGGTCGCTGCCCCAGTCGTC
gb|EU128526.1|     ------------------------------------------------------------
gb|EU034646.1|     GGACACGGCGTCGCTGTCGCTGCCGCTCCAGTTGTCGCCAAGGTCGCTGCCCCAGTCGTC
                   ************************************************************

TROSPA-Salp15      GCTGTCGGCCACGGCGGCTACGGTGGCTACGGACACGGTGGTTTCCTCGGCGGATACGGA
gb|EU128526.1|     ------------------------------------------------------------
gb|EU034646.1|     GCTGTCGGCCACGGCGGCTACGGTGGCTACGGACACGGTGGTTTCCTCGGCGGATACGGA
                   ************************************************************

TROSPA-Salp15      GGTTACGGACACGGAGGATTCGGCGGCTACGGTCTCGGCCACGGCGTCGCTGTCCATGCT
gb|EU128526.1|     ------------------------------------------------------------
gb|EU034646.1|     GGTTACGGACACGGAGGATTCGGCGGCTACGGTCTCGGCCACGGCGTCGCTGTCCATGCT
                   ************************************************************

TROSPA-Salp15      GCCCCAGTTGTCGCCAAGGTCGCTGCCCCAGTCGTCGCTGTCGGCCACGGCTACGGAGGC
gb|EU128526.1|     ------------------------------------------------------------
gb|EU034646.1      GCCCCAGTTGTCGCCAAGGTCGCTGCCCCAGTCGTCGCTGTCGGCCACGGCTACGGAGGC
                   ************************************************************

TROSPA-Salp15      TTCGGTTACGGCGGATATGGCGGACACGGCTACGGACACTAAGCAATTCATCTCAAAGGG
gb|EU128526.1|     ------------------------------------------------------------
gb|EU034646.1|     TTCGGTTACGGCGGATATGGCGGACACGGCTACGGACACTAAGCAATTCATCTCAAAGGG
                   ************************************************************

TROSPA-Salp15      AAACCAACACTTCTTCGCCGCTTCTTATTTATGCGCTTGGGCCGACCAGAGCGCCGCTGG
gb|EU128526.1|     ------------------------------------------------------------
gb|EU034646.1|     AAACCAACACTTCTTCGCCGCTTCTTATTTATGCGCTTGGGCCGACCAGAGCGCCGCTGG
                   ************************************************************

TROSPA-Salp15      AAGTGAAGCGGCGGCGAAAGAAGCGGCGGCGAAAGAAGCGGCGGCGAAAGAAGCGGCGGC
gb|EU128526.1|     ------------------------------------------------------------
gb|EU034646.1|     AAGTTGA-----------------------------------------------------
                   **** **

TROSPA-Salp15      GAAAGAAGCGGCGGCGAAAGAAAACCTGTATTTTCAGGGAATGGAAAGCTTTGTTGCCAT
gb|EU128526.1|     ----------------------------------------ATGGAATCTTTCGTCGCAAT
gb|EU034646.1|     ------------------------------------------------------------
                                                           ^^^^^^   ^^ ^^ ^^ ^^

TROSPA-Salp15      GAAAGTTGTTTGCATTACCGTGCTGTTTGTTATTGTTGCCGTTAATGAAAGCGCAACCAG
gb|EU128526.1|     GAAGGTGGTGTGCATAACAGTTTTGTTTGTTATTGTCGCTGTGAATGAAAGCGCCACAAG
gb|EU034646.1|     ------------------------------------------------------------
                   ^^^ ^^ ^^ ^^^^^ ^^ ^^  ^^^^^^^^^^^^^ ^^ ^^ ^^^^^^^^^^^ ^^ ^^
```

Fig. 3A

```
TROSPA-Salp15      CGAAGCACGTACCAGCAGCGCAGCAAAAGAAACCAAAAAAAAAAATGTGACCCTGCATTT
gb|EU128526.1|     CGAAGCAAGGACATCAAGCGCTGCCAAAGAGACGAAGAAAAAAAATGTGACACTTCACTT
gb|EU034646.1|     ------------------------------------------------------------
                   ^^^^^^^ ^ ^^    ^^^^^ ^^ ^^^^^ ^^ ^^ ^^^^^^^^^^^^^ ^^ ^^ ^^

TROSPA-Salp15      TCCGAGCTATATCCGTAATCCGCAGAAACTGGCACTGGAACTGCTGGAAATTTGCAAAAA
gb|EU128526.1|     CCCCAGTTATATTCGTAACCCCCAAAAACTTGCCCTGGAACTTCTGGAAATTTGCAAAAA
gb|EU034646.1|     ------------------------------------------------------------
                    ^^ ^^ ^^^^^ ^^^^^ ^^ ^^ ^^^^^ ^^ ^^^^^^^ ^^^^^^^^^^^^^^^^^

TROSPA-Salp15      TAATAAAAGCCGCAATAGCCTGCCGAGCACCAATTATAGCGCCATTAATGATAAATATGT
gb|EU128526.1|     TAACAAATCTCGTAACTCCCTTCCTTCCACTAATTACAGTGCGATAAACGACAAATACGT
gb|EU034646.1|     ------------------------------------------------------------
                   ^^^ ^^^   ^^ ^^    ^^^ ^^    ^^^ ^^^^^ ^^ ^^ ^^ ^^ ^^ ^^^^^ ^^

TROSPA-Salp15      GGATTTTAAAAATTGCACCTTTCTGTGCAAACATGCCGAAGATCGTAATGTTACCCTGGA
gb|EU128526.1|     GGACTTCAAGAACTGTACATTTCTCTGCAAACATGCAGAGGATAGAAATGTTACACTGGA
gb|EU034646.1      ------------------------------------------------------------
                   ^^^ ^^ ^^ ^^ ^^ ^^ ^^ ^^^^^ ^^^^^^^^^^ ^^ ^^^ ^ ^^^^^^^ ^^^^^

TROSPA-Salp15      TCTGCCTCCGAATACCCTGTGTGGTCCGAATGGTGAAACCTGTGCAGAAAAAAGCAAATG
gb|EU128526.1|     TCTGCCACCAAACACGCTTTGTGGACCGAATGGAGAGACATGCGCTGAAAAGAGTAAATG
gb|EU034646.1|     ------------------------------------------------------------
                   ^^^^^^ ^^ ^^ ^^ ^^ ^^^^^ ^^^^^^^^ ^^ ^^ ^^ ^^^^^ ^^ ^^^^^

TROSPA-Salp15      CGTTGGTCATATTCCGGGTTGTTAA-----------------------------------
gb|EU128526.1|     CGTTGGGCACATTCCTGGATGTTAGCGCTCCCCCGGCCACCTTTCAGCCAGGAAGACGTG
gb|EU034646.1|     ------------------------------------------------------------
                   ^^^^^^ ^^ ^^^^^ ^^ ^^^^^

TROSPA-Salp15      ------------------------------------------------------------
gb|EU128526.1|     ATTTAATCGACTTAAATCAACCAACAAAGAGCGTTATCAGAACTTCATGAGAAGCGGCTG
gb|EU034646.1      ------------------------------------------------------------

TROSPA-Salp15      ------------------------------------------------------------
gb|EU128526.1|     ATGTATTTATCACGAAATGTAATCTTACTTTTAATAAAATATATTTACATAACGTCAAAA
gb|EU034646.1|     ------------------------------------------------------------

TROSPA-Salp15      ----------
gb|EU128526.1|     AAAAAAAAAA
gb|EU034646.1|     ----------
```

Fig. 3B

TROSPA mrgshhhhhhgmasmtggqqmgrdlyddddkdhpftMAAMEAMAVDMEAMAAAMAAAMVAT
DTVASSAASAMATEATVAMDTASLSLPLQLSPRSLPQSSLSATAATVATDTVVSSADTEVT
DTEDSAATVSATASLSMLPQLSPRSLPQSSLSATATEASVTADMADTATDTKQFISKGNQH
FFAASYLCAWADQSAAGS

TROSPA-Salp15 mrgshhhhhhgmasmtggqqmgrdlyddddkdhpftMAAMEAMAVDMEAMAAAMAAAMVAT
DTVASSAASAMATEATVAMDTASLSLPLQLSPRSLPQSSLSATAATVATDTVVSSADTEVT
DTEDSAATVSATASLSMLPQLSPRSLPQSSLSATATEASVTADMADTATDTKQFISKGNQH
FFAASYLCAWADQSAAGS*EAAAKEAAAKEAAAKEAAAKEAAAK*ENLYFQG*MESFVAMKVVC*
*ITVLFVIVAVNESATSEARTSSAAKETKKKNVTLHFPSYIRNPQKLALELLEICKNNKSRN*
*SLPSTNYSAINDKYVDFKNCTFLCKHAEDRNVTLDLPPNTLCGPNGETCAEKSKCVGHIPG*
*C*

Fig. 5

Fig. 6A
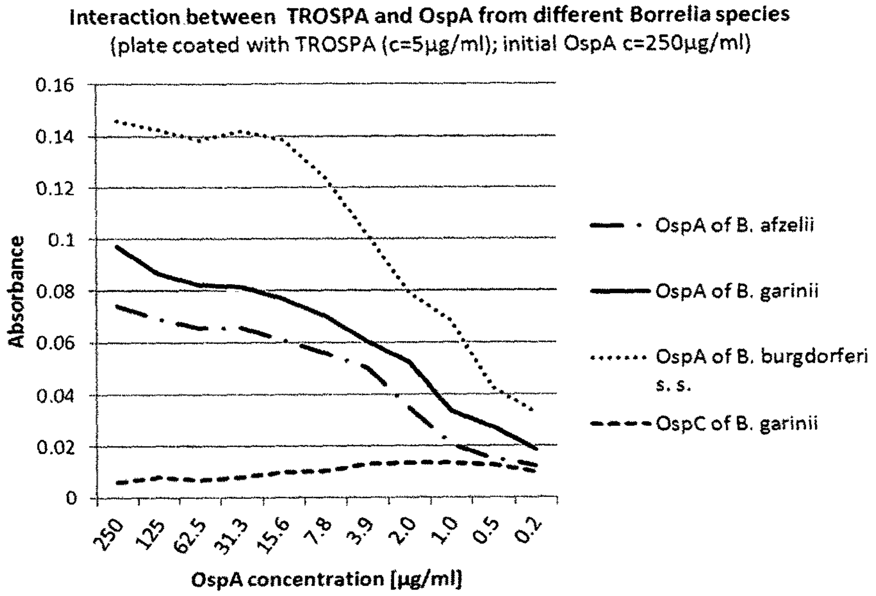
Fig. 6B
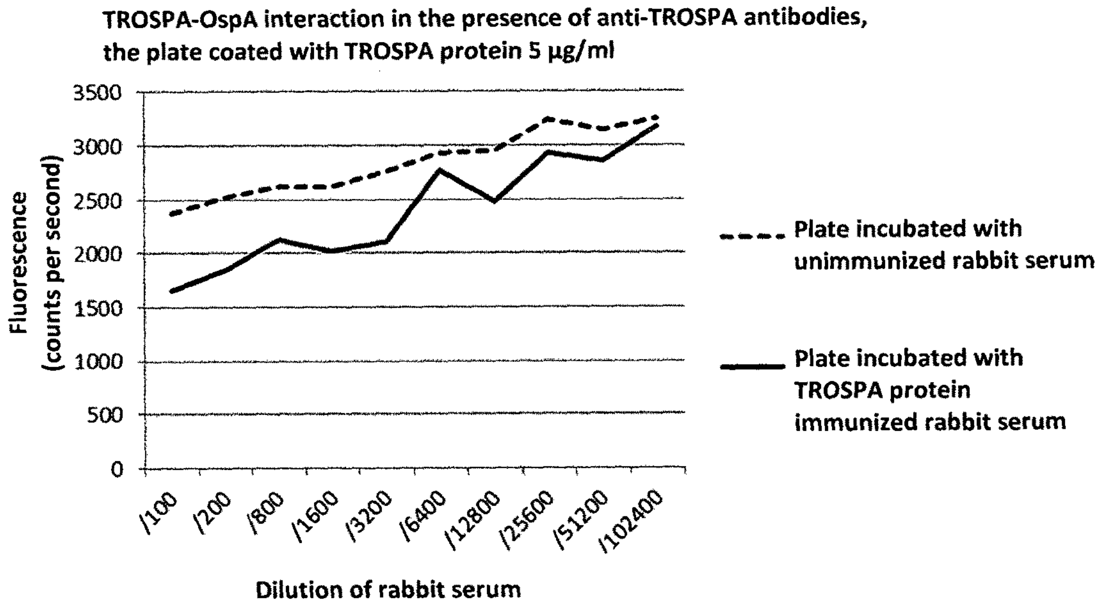
Fig. 6

Fig. 7A
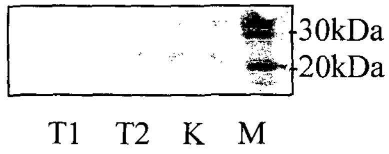
Fig. 7B
Fig. 7C
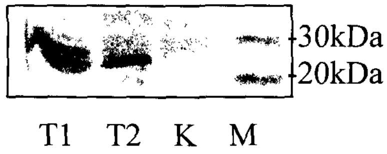
Fig. 7D
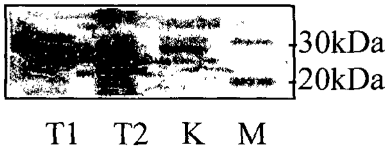
Fig. 7

Fig. 8A

Level of IgG rats immunized with 200μg of recombinant TROSPA or TROSPA-Salp15 protein,
the plate coated with 5 μg/ml of TROSPA protein,
confidence coefficient = 95%

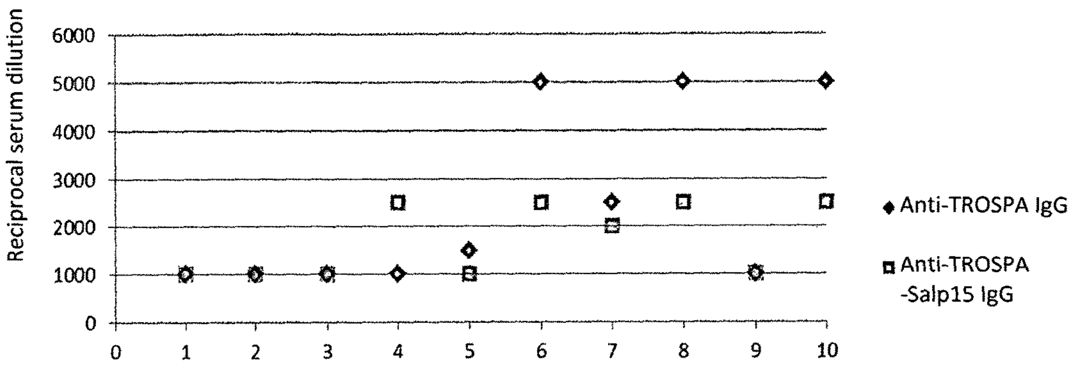

1-5 animals immunized with adjuvant-free preparation
6-10 animals immunized with a preparation containing adjuvant

Fig. 8B

Level of IgG in the serum of rats immunized with 200μg of TROSPA-Salp15 protein,
the plate coated with 5μg/ml of Salp15 protein,
confidence coefficient = 95%

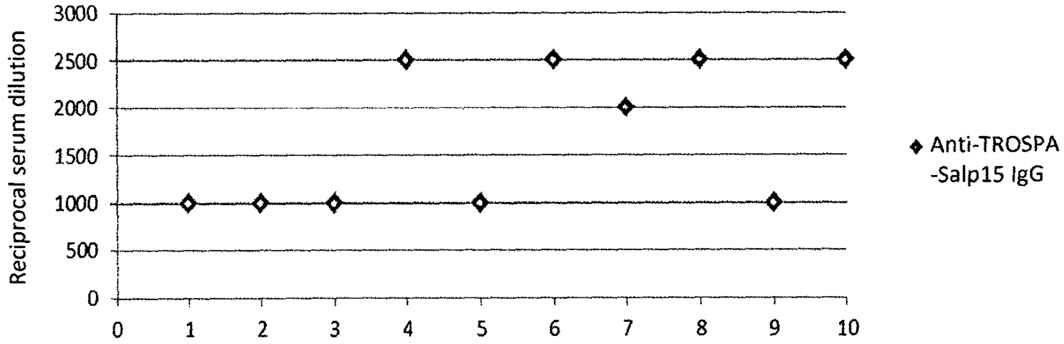

1-5 animals fed with adjuvant-free preparation
6-10 animals fed with a preparation containing adjuvant Level of IgG in the serum of rats immunized with 200μg of TROSPA, OspA, and OspC protein,
the plate caoted with 5 μg/ml of TROSPA, OspA, or OspC protein,
confidence coefficient = 95%

1-5 animals fed with adjuvant-free preparation
6-10 animals fed with a preparation containing adjuvant Invitrogen™
life technologies

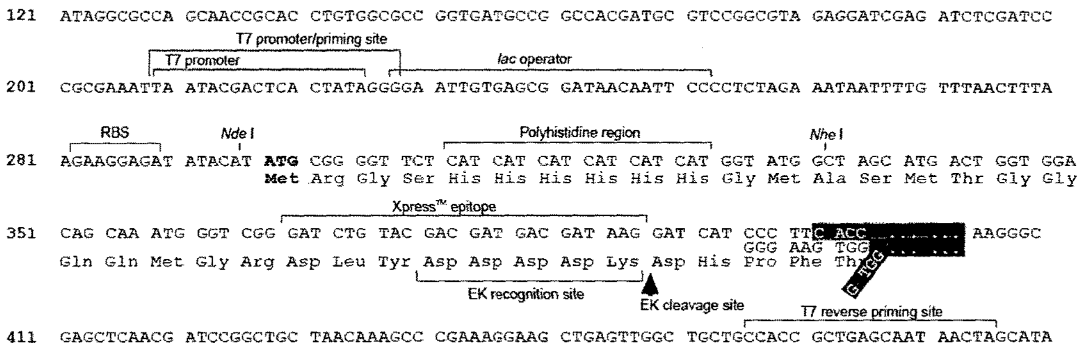

Fig. 9

```
121  ATAGGCGCCA GCAACCGCAC CTGTGGCGCC GGTGATGCCG GCCACGATGC GTCCGGCGTA GAGGATCGAG ATCTCGATCC
                      T7 promoter/priming site
              T7 promoter                        lac operator
201  CGCGAAATTA ATACGACTCA CTATAGGGGA ATTGTGAGCG GATAACAATT CCCCTCTAGA AATAATTTTG TTTAACTTTA
          RBS       Nde I                    Polyhistidine region              Nhe I
281  AGAAGGAGAT ATACAT ATG CGG GGT TCT CAT CAT CAT CAT CAT CAT GGT ATG GCT AGC ATG ACT GGT GGA
                      Met Arg Gly Ser His His His His His His Gly Met Ala Ser Met Thr Gly Gly
                                     Xpress™ epitope
351  CAG CAA ATG GGT CGG GAT CTG TAC GAC GAT GAC GAT AAG GAT CAT CCC TTC ACC              AAGGGC
                                                                         GGG AAG TGG
     Gln Gln Met Gly Arg Asp Leu Tyr Asp Asp Asp Asp Lys Asp His Pro Phe Thr
                                    EK recognition site         EK cleavage site    T7 reverse priming site
411  GAGCTCAACG ATCCGGCTGC TAACAAAGCC CGAAAGGAAG CTGAGTTGGC TGCTGCCACC GCTGAGCAAT AACTAGCATA
```

LYME DISEASE VACCINE, GENETIC CONSTRUCT, RECOMBINANT PROTEIN, METHOD FOR DESIGNING GENETIC CONSTRUCT, METHOD FOR PRODUCING VACCINE, METHOD FOR PRODUCING RECOMBINANT PROTEINS, USE OF RECOMBINANT PROTEINS IN THE PRODUCTION OF LYME DISEASE VACCINE

The present invention relates to Lyme disease vaccine, a genetic construct, recombinant protein, method for designing genetic construct, method for vaccine delivery, method for producing recombinant proteins, use of recombinant proteins in the production of Lyme disease vaccine. In particular, the method concerns the use of TROSPA and TROSPA-Salp15 recombinant proteins derived from castor bean tick (*Ixodes ricinus*) as a component of Lyme disease vaccine for animals. The antibodies present in blood of an immunized vertebrate directed against the TROSPA proteins considerably reduce the chance of infecting new ticks by blocking or hindering the interaction of TROSPA protein with OspA protein of *Borrelia burgdorferi* sensu lato. This interaction is crucial for colonization of tick vector by the spirochete. The antibodies directed against the TROSPA-Salp15 protein additionally protect vertebrates from infection on the stage of *Borrelia* entering the host by destroying their protective coating formed at bacterial surface as a result of the interaction between the Salp15 tick protein and OspC spirochete protein. The vaccine based on TROSPA tick proteins and TROSPA-Salp15 proteins may be used independently or together with the OspA and OspC recombinant proteins from *Borrelia burgdorferi* sensu lato.

Ticks are external parasites living on vertebrates' blood. During their life-cycle, ticks feed on several hosts, which creates an opportunity to transmit different pathogenic microorganisms between the hosts.

An example of such microorganism is *Borrelia burgdorferi* spirochete that causes Lyme disease. The spirochete enters a tick at the larval or nymphal stage, during their feeding on an infected vertebrate. A group of animals that are competent hosts for the spirochete (i.e., animals for which the infection remains permanent) constitute a natural reservoir of *B. burgdorferi*. This group includes rodents and other small mammals and birds (1, 2, 3, 4, 5), while humans and livestock are occasional hosts for *B. burgdorferi.*

For the past decade, there has been a rapid increase of Lyme disease incidence rate in Poland and Europe. According to the data of the Department of Epidemiology of the National Institute of Public Health, the situation in Poland is alarming as they show a tenfold increase of the incidence rate during the past decade, from around 2 to 10 cases of infection per 100 000 people (FIG. 1—Diagram 1). Similar situation has been observed for other European countries.

Lyme disease is not typically a lethal disease; however, the quality of life of the infected individuals is considerably lower than in case of diabetes, heart disease, depression, arthrosis or rheumatoid disease patients. Furthermore, Lyme disease has a destructive influence on domestic animals and livestock, which causes losses in agriculture. As the number of infections with *B. burgdorferi* increases, it is necessary to prevent further spread of the dangerous pathogen. Currently, the most common method of prevention used worldwide, and the only one used in Poland, is education of those exposed to contact with ticks. In general, it consists in encouraging to wear protective clothing or use tick deterrents and instructing on how to act in case of a tick bite. However, according to the data from the USA, the effectiveness of wearing protective clothing is 40%, and in case of tick deterrents use it is 20% (6, 7, 8). Vaccination for humans and animals could be an effective method for Lyme disease prevention. An attempts to develop a vaccine are being made in Europe and USA. The only vaccine allowed for the 3$^{rd}$ phase of clinical trial and, consequently, approved by the FDA was Lymerix—that entered the U.S. market in 1998 (9, 10, 11). An active ingredient of the vaccine was the OspA surface recombinant protein *B. burgdorferi* sensu stricto. The antibodies directed against OspA neutralize the bacteria present in the tick gut, which prevents human infection. Nevertheless, the vaccine was withdrawn by the manufacturer in 2002 due to poor demand, high price and rheumatological side effects (*arthralgia*) that had appeared for a few individuals after using Lymerix, as officially stated. The possible side effects were associated with the fact that the OspA protein includes an antigen homologous to human LFA-1 antigen (Lymphocyte function-associated antigen 1), which, in case of immunization with OspA protein, may result in autoimmune response of an organism (12, 13, 14). A vaccine based on OspA administered in three doses showed a considerably high effectiveness of 79% at the 3$^{rd}$ phase of clinical trial (11). In the USA, the vaccines based on OspA recombinant protein for domestic animals are still available (15).

A more comprehensive approach to Lyme disease prevention could involve the introduction of prophylactic vaccination of wild animals that constitute a reservoir of *Borrelia*, This would decrease the number of infections with *B. burgdorferi*. One of the research groups in the USA is working on an OspA protein-based vaccine for wild animals that applies the *Vaccinia* virus, similarly as in case of rabies vaccine. A product has been prepared in the form of feed that included a harmless, modified *Vaccinia* virus carrying in its DNA a gene coding for OspA. An expression of the virus genes and OspA protein has been shown for the mice treated with the product. The presence of OspA in mouse organism resulted in the development of anti-OspA antibodies to the level that conferred effective protection against infection with *B. burgdorferi* in laboratory conditions (16).

In Europe, Lyme disease prevention is even more complicated as the vaccine against *B. burgdorferi* manufactured in the USA, based on its surface protein, is ineffective. This is a consequence of serological disparities among the bacteria strains occurring in different geographical regions, which is due to the fact that the *B. burgdorferi* surface proteins are encoded by plasmid DNA that is high variable. Therefore, attempts are being made to find an alternative solution for the vaccines based on bacterial surface proteins. Recently, an interesting paper has been published that presents protective features of the Salp15 tick protein (17). The protein occurs in tick saliva. It interacts with the OspC surface protein of *B. burgdorferi* and forms a protective coating on the surface of the bacteria to inhibit the recognition of the bacteria by the immune system of the infected vertebrate. The laboratory animals immunized with the recombinant Salp15 protein revealed considerable resistance to *B. burgdorferi* infection. Also, it was shown that the enrichment of the previously developed vaccines based on OspA and OspC surface proteins with the Salp 15 protein considerably improved protection against the infection.

Intensive studies that aim at the development of a human vaccine against the infection with *B. burgdorferi* are still being carried out.

The US2007020286 patent application describes a chimeric recombinant protein that is a combination of the OspA and OspC proteins of *B. burgdorferi* as a possible vaccine against Lyme disease. The solution presents new chimeric nucleic acids, coding the chimeric OspC protein of *Borrelia* or its antigen fragment and the chimeric OspA protein or its antigen fragment. Furthermore, chimeric proteins coded by nucleic acids sequences are shown. Chimeric proteins may be used as immunogens of a vaccine against Lyme disease or in immunodiagnostic reagents.

The US2012020973 patent application describes a chimeric recombinant protein that is a combination of the antigens of OspA proteins of different *Borrelia burgdorferi* sensu lato as a possible vaccine against Lyme disease. The invention relates to the molecules of chimeric OspA protein that may be applied in new vaccines against Lyme disease. In particular, the chimeric OspA proteins comprise a proximal part of one OspA serotype together with a distal part of another OspA serotype, and maintain the antigen features of both initial proteins. Chimeric OspA molecules are delivered separately or combined so as to ensure protection against various *Borrelia* strains. The solution also presents the ways of providing the chimeric OspA molecules to the object that is to be protected and cured in case of Lyme disease or *Borrelia.*

The WO2008063240 patent application presents the preparation of a vaccine using the *Lactobacillus* bacteria that produces an OspA protein of *Borrelia burgdorferi*. The invention relates to the *Lactobacillus* bacteria where 1) a recombinant peptide is expressed that comprises a signaling lipoprotein sequence of OspA protein of *Borrelia burgdorferi* or an active variant of a leader sequence attached to one or more indicated heterologous polypeptides and/or 2) comprises a polynucleotide that undergoes gene expression, coding for recombinant polypeptide having a lipoprotein signal from the OspA protein of *Borrelia burgdorferi* or its active variant attached to one or more indicated heterologous peptides. According to the invention, one of the solutions involves a heterologous polypeptide derived from *Yersinia pestis* (the Plague *bacillus*), an ethiologic factor of the Plague. In the other solution, the heterologic polypeptide is derived from *Borrelia burgdorferi*, ethiologic factor of Lyme disease. Moreover, immunogenic compositions are described, including vaccines with live bacteria, ways of obtaining immunologic response directed against polypeptides, and the compositions that include bacteria.

The CZ301244 patent describes the preparation of a vaccine product based on lysate from *Borrelia burgdorferi* sensu stricto, *Borrelia afzelii*, and *Borrelia garinii*. The invention relates to a general application vaccine for the treatment and prevention of Lyme disease in humans and animals, based on bacterins formed on the basis of whole cells, bacterial lysates or purified products derived from the three most pathogenic genome species of *Borrelia* selected from: *Borrelia burgdorferi* sensu stricto, *Borrelia afzelii* and *Borrelia garinii*, comprising at least one immunogenic protective protein from the outer membrane of both OspA or OspC, or, at the same time, immunogenic protective protein from the OspA and OspC outer membrane or other immunogenic protective proteins from the outer membrane. Also, a method for the production of the above-mentioned vaccine was presented therein.

The US2003138868 patent presents a number of factors of *Borrelia burgdorferi* sensu lato that are potentially relevant in prevention of Lyme disease. The solution concerns the agents for diagnosing and/or treating of Lyme disease that comprise the antigens of glyceraldehydephosphate dehydrogenase (GAPDH), oligopeptide permease, oligopeptide ABC transporter periplasmic BP (oppA-2)(Bb), glycoside transpherase IgtD homologue, heat-shock protein 90, VLSE fragment, (U76406) putative v1s rec. cassette V1 s6 *Borrelia burgdorferi*, flagellin protein *Borrelia garinii*, (AE001578) conserved hypothetical protein cp32-6 *Borrelia burgdorferi*, membrane assoc. protein p66 precursor *Borrelia burgdorferi*, oligopeptide ABC transporter periplasmic BP (oppA-4)(Bc), fructose-biphosphate aldose (fba) *Borrelia burgdorferii*, DNAK protein, heat-shock protein 70 *Borrelia burgdorferi*, orfE *Borrelia burgdorferi*, outer surface protein B precursor *Borrelia burgdorferi*, L-lactate dehydrogenase (ldh), P83/100 gene *Borrelia burgdorferi*, enolase 2-phosphoglycerate *Borrelia burgdorferi*, flagellin protein *Borrelia garinii*, hypothetical protein BBE28 *Borrelia burgdorferii*, DNA direct. RNA polymerase (rpoA) homologue, P66 protein (fragment), flagellin (fragment), DNA direct. RNA polymerase, integral outer membrane protein p66, pyruvate kinase (pyk) homologue), kinase (pgk) and/or BBU28760 NID and/or fragments thereof and/or the nucleic acid sequences encoding said antigens and/or said fragments.

The PL 169804 patent describes a method to produce a vaccine against Lyme disease based on antibodies specific for OspA or OspB *Borrelia burgdorferi* protein. The object of invention is a vaccine against Lyme disease that comprises one or more monoclonal antibodies specific for 31 kD (OspA) antigen or 34 kD(Osp B) antigen *Borrelia burgdorferi*, the method to obtain the vaccine by the fusion of lymphocytes or spleen cells with the formation of hibridoma that produces a monoclonal antibody. The object of invention is also an LA2 monoclonal antibody against OspA, LA26.1 against OspA, LA 25.1 against OspB, LA 27.1 against OspB, pathogenic strain *B. burgdorferi* ZS7, DSM 5527, an antigen causing immunological reaction with an antibody against OspA, against OspB, recombinant DNA and recombinant vector, the method to obtain antigens, a vaccine that provides active immunization against Lyme disease, the method to obtain Lyme disease vaccine through studies on immunized animals, and a method for isolation and recultivation of *B. burgdorferi* pathogenic cells, from immunodefective laboratory animals.

Despite several proteins have been proposed to play role in the invention of Lyme disease vaccine, it was only OspA *B. burgdorferi* that has been approved for the 3$^{rd}$ phase of clinical trials (15). The serologic differences occurring among the bacteria strains of various geographical regions, that result from the fact that *B. burgdorferi* s. l. surface proteins are coded by high variable plasmid DNA, are the cause of a continuous search for an alternative to the vaccines based on surface proteins of *B. burgdorferi.*

The TROSPA protein occurs on the surface of tick gut and participates in the process of *B. burgdorferi* s. l. entering the vector. It is the OspA protein of the spirochete that participates in this interaction (18). The Salp15 protein is present in tick saliva. It interacts with a surface OspC protein of *B. burgdorferi* s. l. and forms a protective coating on the bacteria surface that inhibits bacteria recognition by immunological system of an infected vertebrate (19). Even though both TROSPA protein and Salp15 protein come from a tick, they play key role in two different phases of *B. burgdorferi* life cycle. The antibodies present in blood of an immunized vertebrate directed against Salp15 protein protect an animal from infection when spirochetes enter the host by destroying the protective coating on the bacteria surface formed through the interaction of Salp 15 and OspC. The laboratory animals immunized with recombinant Salp 15 protein revealed considerable immunity to the infection with *B. burgdorferi*. Moreover, it was showed that enrichment of the previously produced vaccines based on recombinant surface OspA and OspC proteins with Salp15 protein significantly increased the effectiveness of protection against the infection with a spirochete (20).

The aim of the invention is to provide a vaccine comprising TROSPA and TROSPA-Salp 15 proteins that show immunogenic properties. The antibodies present in blood of an immunized vertebrate directed against TROSPA proteins significantly lower the chance of infecting new ticks by blocking or inhibiting the interaction of TROSPA and OspA. This reduces the natural reservoir of bacteria, which results in lower incidence of Lyme disease in humans and animals. Furthermore, the antibodies present in blood of an immunized vertebrate directed against Salp15 antigen of TROSPA-Salp15 fusion protein protect an animal against infection on the spirochetes entering stage through destroying the protective coating on the bacteria surface formed by the Salp15 and OspC interaction. The vaccine based on TROSPA protein and TROSPA-Salp15 protein may be used separately or combined with. OspA and OspC proteins of *Borrelia burgdorferi* sensu lato.

The proposed solutions enable obtaining a vaccine against Lyme disease that comprises recombinant TROSPA and TROSPA-Salp15 proteins having immunogenic properties.

The present invention relates to a vaccine against Lyme disease based on TROSPA and TROSPA-Salp15 tick proteins characterised in that it comprises recombinant TROSPA protein defined by sequence SEQ. ID No. 3 or recombinant TROSPA-Salp 15 protein defined by SEQ. ID sequence No. 4.

Preferably, the vaccine comprises a protein obtained by the expression of the TROSPA genetic construct defined by sequence SEQ. ID No. 1 or recombinant protein obtained by the expression of the TROSPA-Salp15 genetic construct defined by sequence SEQ. ID No.2.

Preferably, the recombinant TROSPA and/or TROSPA-Salp15 protein have immunogenic properties.

Preferably, the vaccine is used separately or combined with OspA and OspC proteins of *Borrelia burgdorferi* sensu lato.

Preferably, the vaccine comprises TROSPA recombinant proteins preparation of *Ixodes ricinus* and OspA and OspC of *Borrelia burgdorferi* sensu lato.

Preferably, it protects an animal against infection on the spirochetes entering.

Preferably, the antibodies present in blood of an immunized vertebrate interact with TROSPA protein in *Ixodes ricinus* gut.

Preferably, the antibodies present in blood of an immunized vertebrate directed against Salp15 proteins interact with the protective coating on the bacteria surface formed through the Salp15 and OspC interaction.

Preferably, the antibodies present in blood of an immunized vertebrate directed against TROSPA proteins block or hinder the interaction of TROSPA and OspA, and the antibodies directed against Salp15 antigen present in TROSPA-Salp15 fusion protein protect an animal against infection on the spirochetes diffusion by destroying the protective coating on the bacteria surface formed by Salp15 and OspC interaction.

Preferably, the antibodies present in blood of an immunized vertebrate directed against TROSPA proteins lower the chance of infecting new *Ixodes ricinus.*

The present invention also relates to TROSPA genetic construct characterised in that it is described by sequence SEQ. ID No. 1.

The present invention also relates to TROSPA-Salp15 genetic construct characterised in that it is described by sequence SEQ. ID No. 2.

The other subject of invention is recombinant TROSPA protein, characterised in that it is a product of the TROSPA genetic construct expression, described by sequence SEQ. ID No 3.

The other subject of invention is recombinant TROSPA-Salp15 protein characterised in that it is a product of the TROSPA-Salp5 genetic construct expression, described by sequence SEQ ID No 4.

Preferably, the recombinant protein has immunogenic properties.

Preferably, the above-mentioned recombinant proteins interact with the OspA protein of *Borrelia burgdorferi* sensu lato.

The next subject of invention is a method of production of the above-mentioned TROSPA genetic construct characterised in that it is obtained by amplifying the gene coding for the TROSPA protein of *I. ricinus* with PCR based on the DNA isolated from *I. ricinus* defined by sequence SEQ. ID No. 5 and sequence SEQ. ID No. 6 starters, next, it is spliced in plant cells and, then, the obtained mRNA TROSPA is amplified by reverse transcriptase and PCR using the sequence SEQ. ID No. 7 and sequence SEQ. ID No. 8 starters, and it is cloned in a pET200/D-TOPO vector.

The next subject of invention is a method of production of the above-mentioned TROSPA-Salp15 genetic construct characterised in that it is obtained through DNA synthesis based on the SEQ. ID No.1 genetic construct and Salp-15 Iric-1 (gb EU128526.1) protein coding sequence, optimized for the expression in a bacterial system, next, the obtained DNA TROSPA-Salp15 sequence defined by SEQ. ID No.2 is amplified by PCR with FUS11Ar starters defined by SEQ. ID No. 9 and FUS11Ar defined by SEQ.ID No. 10, and it is cloned in a pET200/D-TOPO vector.

The next subject of invention is a method to produce the above-mentioned vaccine characterised in that it is obtained through SEQ. ID No. 1 or SEQ. ID No. 2 gene construct expression in *E. coli.*

The next subject of invention is a method for producing the above-mentioned recombinant proteins characterised in that it is obtained through SEQ. ID No. 1 or SEQ. ID No. 2 gene construct expression in *E. coli.*

The next subject of invention is the use of the above-mentioned recombinant TROSPA and TROSPA-Salp15 proteins from a castor bean tick (*I. ricinus*) to produce a vaccine against Lyme disease for animal immunization.

Preferably, the composition comprising the purified recombinant TROSPA protein defined by SEQ. sequence No. 3 is administered parenterally.

Preferably, when the composition comprising the purified recombinant protein defined by SEQ. sequence No. 3 or SEQ. protein No. 4 is administered orally.

Preferably, the composition comprising the purified recombinant protein defined by SEQ. sequence No. 3 and the recombinant OspA and OspC proteins of *Borrelia burgdorferi* sensu lato is administered orally.

FIG. 1 presents Lyme disease incidence rate in Poland according to the National Institute of Public Health.

Figure 4:
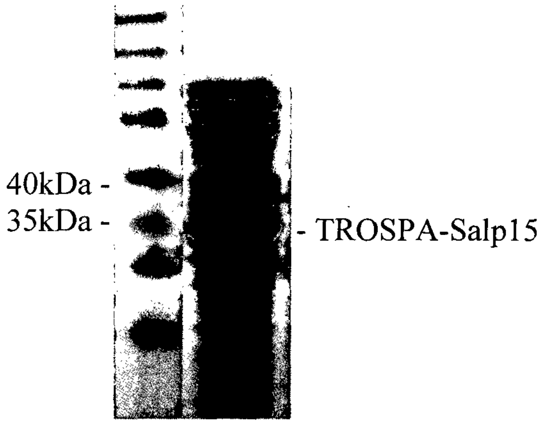

To facilitate better understanding of the discussed issues, the solutions are presented in the figures, where:

FIG. 2 presents the selected phases of preparation and expression of the genetic construct coding for the recombinant TROSPA protein. Fig A - DNA electrophoretic analysis: TROSPA gene amplified with PCR on the basis of the DNA isolated from *I. ricinus* (g), TROSPA cDNA amplified with PCR from RNA isolated from *N. benthamiana* agroinfiltrated with a construct comprising the TROSPA gene (w). Fig B - electrophoretic analysis of the purified recombinant TROSPA protein produced in *E. coli* (T), size marker (w). Fig C shows a comparison of a publically available GenBank EUO34646.1 nucleotide sequence of *Ixodes ricinus* TROSPA mRNA (as mentioned in the Figure description) and the sequence of a genetic construct of SEQ ID NO: 1 coding for the TROSPA recombinant protein. Conservative nucleotides were marked with "*", nonconservative nucleotides are put in bold italics;

FIG. 3 shows a comparison of the nucleotide sequence of a genetic construct of SEQ ID NO: 2 coding for the recombinant TROSPA-Salp15 protein and the relevant sequences of Ixodes ricinus Salp15 Iric-1 mRNA, complete cds GenBank: EU128526.1 and *Ixodes ricinus* TROSPA mRNA complete cds GenBank No. EUO34646.1, the nucleotides identical for the sequences coding the recombinant TROSPA-Salp15 protein and *Ixodes ricinus* TROSPA mRNA complete cds GenBank No. EUO34646.1 are marked with ,*", the nucleotides identical for the sequences coding the recombinant TROSPA-Salp 15 protein and *Ixodes ricinus* Salp15 Iric-1 mRNA complete cds GenBank No. EU128526.1 are marked with ,$^{A}$", FIG. 3 comprises FIGS. 3A and 3B wherein 3A continues to 3B;

FIG. 4 presents the electrophoretic analysis of purified recombinant TROSPA-Salp15 protein obtained for *E. coli;*

Figures 8, 8C:
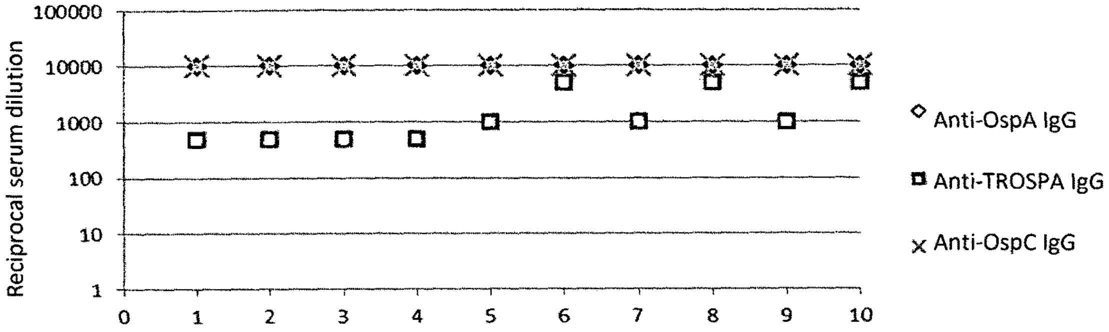

FIG. 5 presents the amino acid sequences of the recombinant TROSPA protein (SEQ ID NO: 3) and TROSPA-Salp15 protein (SEQ ID NO: 4) (the fragment coding for a protein label of pET200/D-TOPO is bolded and put in lowercase, the fragment coding for the TROSPA sequence is underlined and bolded, the fragment coding for the Salp15 is underlined and put in italics, the site recognized by TEV protease is underlined);

FIG. 6 presents the influence of the recombinant OspA protein concentration on the complex formation between the TROSPA recombinant protein from *Ixodes ricinus* and OspA recombinant proteins from three different *Borrelia* species (i.e. *B. garinii, B. afzelii* and *B. burgdorferi* sensu stricto); FIG. 6A—complex formation between TROSPA and OspA proteins of *B. garinii, B. afzelii*, or *B. burgdorferi* s. s. The interaction was analyzed on an ELISA microplates coated with recombinant. TROSPA protein and incubated with serial dilutions of recombinant OspA proteins (either from *B. garinii, B. afzelii* or *B. burgdorferi* s. s.). As a control, analogous assays with OspC from *B. garinii* were performed. The detection of the bound protein was carried out using a commercially available primary *Borrelia*-specific antibodies (rabbit polyclonal IgG) and secondary antibodies (anti-rabbit polyclonal IgG) conjugated with alkaline phosphatase. Absorbance of the soluble product of the alkaline phosphatase reaction was measured by using the Microplate Reader Model 550 (BIORAD);

FIG. 6B—comparison of the efficiency in complex formation between the recombinant TROSPA and OspA proteins (of *B. garinii*) in the presence of serum from rabbit immunized with recombinant TROSPA protein. In the control reaction the preimmune rabbit serum was applied. The interaction was analyzed on ELISA microplate coated with recombinant TROSPA protein. The plates were incubated with serial dilutions of immunized and preimmune rabbit serum and, then, with recombinant OspA protein at the concentration of 80 μg/ml. The detection of the bound recombinant OspA protein was carried out using the anti-*Borrelia* antibodies conjugated with FITC, and the fluorescence was measured using the VICTOR X4 2030 Multilabel Reader by PerkinElmer;

FIG. 7 presents the analysis of the specificity of anti-TROSPA antibodies produced in rabbit after parenteral immunization with the recombinant TROSPA protein preparation. The animals were given 100 μg of the preparation at four time points: on 0, 14, 28, and 56th day. The serum was taken before immunization (FIG. 7A) and, then, 38 (FIG. 7B), 66 (FIG. 7C), and 87 days (FIG. 7D) after immunization. The presence of antibodies in the serum of the immunized animals was detected by the Western-blot analysis, using the anti-rabbit antibodies conjugated with alkaline phosphatase. T1—purified TROSPA protein, T2—lysate from bacteria producing TROSPA protein, K—lysate from bacteria producing other protein (recombinant OspC protein of *B. burgdorferi*), M—mass marker;

FIG. 8 presents the level of IgG in the serum of rats immunized with recombinant TROSPA, TROSPA-Salp15 or TROSPA, OspA and OspC proteins; FIG. 8A—a microplate coated with recombinant TROSPA protein was incubated with increasing dilutions of the serum of animals orally immunized with the recombinant TROSPA or TROSPA-Salp15 protein preparation; FIG. 8B—a microplate coated with recombinant Salp15 protein was incubated with increasing dilutions of the serum of animals orally immunized with the TROSPA-Salp15 protein preparation; FIG. 8C—a microplate coated with one of the recombinant proteins: TROSPA, OspA or OspC was incubated with increasing dilutions of rats orally immunized with TROSPA OspA and OspC protein preparation. Next, the detection of the level of the bound rat IgG was carried out using the commercially available anti-rat antibodies conjugated with alkaline phosphatase. Maximum dilution rates of the immunized animals' serum are marked for which statistically significant difference was found in comparison with the control group of the animals immunized with an adjuvant only.

FIG. 9 presents a schematic description of the cloning site of a commercially available pET200/D expression vector by Invitrogen, Carlsbad, California, USA. This vector contains the Xpress™ epitope and the 6×His tag that has been cloned N-terminally in frame with the protein of interest. N-terminal tags can be 20 removed by enterokinase cleavage.

In order to better understand the invention, sample solutions are following.

EXAMPLE 1

The production of recombinant TROSPA tick protein defined by SEQ ID No. 3 and TROSPA-Salp15 defined by SEQ ID No. 4, and recombinant OspA proteins of *B. garinii, B. afzelii* and *B. burgdorferi* s. s., and OspC protein of *B. garinii*; a study of interaction between the recombinant TROSPA tick protein and recombinant OspA proteins of *B. garinii, B. afzelii*, and *B. burgdorferi* s. s.

The TROSPA gene was amplified by PCR on the basis of genomic DNA isolated from *I. ricinus* collected in Poland, using the DNA QIAamp DNA Mini Kit by QIAGEN. For the PCR amplification, the TROSPAF and TROSPAR (Table 1) starters were used, defined by sequence SEQ ID No. 5 and sequence SEQ ID No. 6, and designed based on the sequence available at GenBank No. EU034646.1. As TROSPA gene comprises one intron, it had to be subjected to splicing. Accordingly, the TROSPA gene was cloned in binary vector, and the obtained construct was used for agroinfiltration of *N. benthamiana*, according to the manufacturer's protocol.

Next, the trospa cDNA was amplified and cloned in a pET expression vector, using the TROTOPF and TRORPST starters defined by sequence SEQ ID No. 7 and sequence SEQ ID No. 8. For the cloning and the subsequent expression of the recombinant TROSPA protein defined by sequence SEQ ID No. 3, the Champion™ pET200 Directional TOPO® Expression Kit with BL21 Star™ (DE3) One Shot® (FIG. 9) was used, according to the manufacturer's protocol. As a result of cloning to pET200/D-TOPO vector, a TROSPA genetic construct was formed defined by sequence SEQ ID No. 1, as shown in FIG. 2C, coding for the recombinant TROSPA protein defined by sequence SEQ ID No. 3. FIGS. 2A and 2B present selected stages of the production and expression of TROSPA genetic construct coding for recombinant TROSPA protein. The recombinant TROSPA protein produced in the above-mentioned bacterial system, defined by sequence SEQ ID No. 3 had a his-tag added at its N terminus (FIG. 9), which allowed for protein purification using affinity chromatography with a nickel column. The elution of the recombinant TROSPA protein was carried out at 200 mM concentration of imidazole. Electrophoretic analysis of the purified TROSPA protein is presented in FIG. 2B. The preparation was dialyzed in a 1× PBS buffer. FIG. 5 shows the aminoacid sequence of the recombinant TROSPA protein.

The DNA TROSPA-Salp15 sequence was obtained through DNA synthesis based on the cloned sequence coding for the recombinant TROSPA protein and a sequence coding for Salp15 Iric-1 protein, published in GenBank No. EU128526.1 that was optimized for the expression in a bacterial system. FIG. 3 presents the nucleotide sequence of the TROSPA-Salp15 genetic construct coding for the recombinant TROSPA-Salp15 protein and the comparison of its relevant fragments with the sequences EU034646.1 and EU128526.1. The DNA TROSPA-Salp15 sequence was amplified by PCR with FUS11Af and FUS11Ar starters defined by SEQ ID No. 9 and SEQ ID No. 10 sequences. Next, the cloning and expression of the TROSPA-Salp15 genetic construct defined by SEQ ID No. 2 was carried out, using the Champion™ pET200 Directional TOPO® Expression Kit with BL21 Star™ (DE3) One Shot® (FIG. 9), according to the manufacturer's protocol. The protein did not bind to the nickel column despite the presence of his-tag at its N terminus (FIG. 9). The purified preparation of the recombinant TROSPA-Salp15 protein was obtained through ion-exchange chromatography, using the DEAE-cellulose bed. The elution of the recombinant TROSPA-Salp15 protein was carried out at 200 mM of NaCl concentration. The electrophoretic analysis of the purified protein is presented in FIG. 4. The protein preparation was dialyzed in a 1× PBS buffer.

The amino acid sequences of the recombinant TROSPA and TROSPA-Salp15 proteins are shown in FIG. 5. The amino acid sequences of the recombinant TROSPA and TROSPA-Salp15 proteins produced in *E. coli* were confirmed by mass spectrometry (MALDI-TOF spectrometer).

The sequences coding for OspA of *Borrelia burgdorferi* sensu lato (i.e. *B. garinii, B. afzelii* and *B. burgdorferi* sensu stricto) and OspC proteins of *B. garinii* were amplified by PCR on the basis of DNA isolated *I. ricinus* collected in Poland, using the DNA QIAamp DNA Mini Kit by QIAGEN. For the PCR amplification, the OspAf/OspAr and OspCf/OspCr starter pairs were used (Table 1), designed on the basis of the sequences available at GenBank: *B. garinii* ospA GenBank: X85441.1, *B. afzelii* ospA GenBank: X85438.1, *B. burgdorferi* s. s. ospA GenBank: X16467.1 *Borrelia garinii* gene for outer surface protein C, complete cds GenBank: D49498.1. The amplified DNA coding for the OspA and OspC proteins (*B. garinii, B. afzelii* and *B. burgdorferi* s. s.) was cloned and subjected to expression with the Champion™ pET200 Directional TOPO® Expression Kit with BL21 Star™ (DE3) One Shot®, according to the manufacturer's protocol. In this way, the recombinant OspA and OspC proteins of *Borrelia burgdorferi* sensu lato were obtained, having protein label at its N-end (supplement 1), which allowed for their purification using affinity chromatography with a nickel column. The elution of the recombinant OspA and OspC proteins was carried out at 200 mM concentration of imidazole. The preparations were dialyzed in a 1× PBS buffer. The amino acid sequences of the recombinant OspA and OspC proteins of *Borrelia burgdorferi* sensu lato were confirmed by mass spectrometry (MALDI-TOF spectrometer).

Moreover, it was found that the recombinant TROSPA protein defined by sequence SEQ ID No. 3 and the OspA recombinant proteins from three different *Borrelia* species (i.e. *B. garinii, B. afzelii* and *B. burgdorferi* sensu stricto) maintained their innate ability to form a TROSPA—OspA complexes. It was confirmed by interaction analysis using ELISA tests. The ELISA microplate was coated with a recombinant TROSPA protein by incubation of the 5 μg/ml protein solution in a PBST buffer. Next, the plate was washed five times with a PBSTT buffer and blocked by incubation in 2% BSA solution in a PBSTT buffer. After the blocking, the plate was washed five times with a PBSTT buffer and incubated with serial dilutions of the recombinant OspA protein (either from *B. garinii, B. afzelii* or *B. burgdorferi* s. s.) and control—OspC protein of *B. garinii*. The detection of the bound protein was carried out using a commercially available primary *Borrelia*-specific antibodies (rabbit polyclonal IgG) and secondary antibodies (anti-rabbit polyclonal IgG) conjugated with alkaline phosphatase. Then, the interaction between the recombinant TROSPA and OspA proteins were compared in the presence of serum of a rabbit immunized with recombinant TROSPA protein. As a control preimmuned rabbit serum was used. For that purpose, the ELISA microplate was coated with recombinant TROSPA protein by incubation of a 5 μg/ml protein solution in a PBSTT buffer. Next, the plate was washed five times with a PBSTT buffer and blocked by incubation in a 2% BSA solution in a PBSTT buffer. After the blocking, the plate was washed five times with a PBSTT buffer and incubated with serial dilutions of the preimmuned rabbit serum or serum from the rabbit immunized with TROSPA. Then, the plate was washed five times with a PBSTT buffer and incubated with 80 μg/ml recombinant OspA protein. The detection of the bound recombinant OspA protein was carried out using commercially available anti-*Borrelia* antibodies conjugated with FITC. The results of the experiment, shown in FIG. 6A, confirmed an ability to form a complex between the recombinant TROSPA protein defined by sequence SEQ ID No. 3 and recombinant OspA proteins from three different *Borrelia* species (i.e. *B. garinii, B. afzelii* and *B. burgdorferi* sensu stricto). Also, an ability to hinder that interaction by anti-TROSPA antibodies was confirmed (FIG. 6B).

TABLE 1

| Nucleotide sequences of the PCR reaction starters. | |
|---|---|
| starter | Nucleotide sequence |
| TROSPAF (SEQ. ID. No. 5) | TTTGGTCTCAAGGTATGGCGGCTATGGAGGC |
| TROSPAR (SEQ. ID. No. 6) | ATATTTAAATTCAACTTCCAGCGGCGC |
| TROTOPF (SEQ. ID. No. 7) | CACCATGGCGGCTATGGAGGC |
| TRORPST (SEQ. ID. No. 8) | ATCTGCAGTCAACTTCCAGCGGCGCTCTGGTCGG |
| FUS11Af (SEQ. ID. No. 9) | CACCATGGCGGCTATGGAGGCTATGGCGG |
| FUS11Ar (SEQ. ID. No. 10) | ATGGATCCTTAACAACCCGGAATATGACCA |
| OspAf (SEQ. ID. No. 11) | CACCATGAAAAAATATTTATTGGGAATAGGT |
| OspAr (SEQ. ID. No. 12) | CCTTATTTTAAAGCGTTTTTA |
| OspCf (SEQ. ID. No. 13) | CACCATGAAAAAGAATACATTAAGTGC |
| OspCr (SEQ. ID. No. 14) | TTAAGGTTTTTTTGGACTTTCTGC |

EXAMPLE 2

Immunization of Animals

A number of studies were performed showing that the recombinant TROSPA protein defined by sequence SEQ ID No. 3 and recombinant TROSPA-Salp15 protein defined by sequence SEQ ID No. 4 have immunogenic properties and may be used as vaccine components. The antibodies present in blood of an immunized vertebrate directed against the recombinant TROSPA protein considerably lower the chance of new ticks infection by blocking or hindering the influence of TROSPA—OspA. In this way, the natural reservoir of bacteria is reduced, which results in lowered incidence rate of Lyme disease among humans and animals. What is more, the antibodies present in blood of an immunized vertebrate directed against Salp15 antigen present in recombinant TROSPA-Salp15 protein protect an animal against infection on the spirochetes entering by destroying the protective coating on the bacteria surface formed through the interaction of Salp15 and OspC, as described herein (18). A vaccine based on recombinant TROSPA and TROSPA-Salp15 proteins defined by sequences SEQ ID No. 3 and SEQ ID No 4 may be used separately or combined with the recombinant OspA and OspC proteins of *Borrelia burgdorferi* sensu lato.

Trademarks Champion™ pET200 Directional TOPO® Expression Kit and BL21 Star™(DE3) One Shot are trademarks for a commercially available expression kit owned by Invitrogen, Carlsbad, California, USA.

A) Immunization of Animals by Parenteral Administration of the Preparation Comprising a Purified Recombinant TROSPA Protein of *Ixodes ricinus* Defined by Sequence SEQ ID No. 3.

An expression of a TROSPA gene construct defined by sequence SEQ ID No. 1 was performed in a bacterial system, using the Champion™ pET200 Directional TOPO® Expression Kit with BL21 Star™ (DE3) One Shot®, according to the manufacturer's protocol. Next, the recombinant TROSPA protein defined by sequence SEQ ID No. 3 was purified using the affinity chromatography with a nickel column. The elution of the recombinant TROSPA protein was carried out at 200 mM concentration of imidazole. The electrophoretic anaysis of the recombinant TROSPA protein is presented in FIG. 2B. The preparation was dialyzed in a 1× PBS buffer. The 800 μg/ml preparation was used for parenteral immunization of rabbits. The animals were given 100 μg of the preparation at four time points: on 0, 14, 28, and 56th day. The serum was taken before the immunization and, then, 38, 66, and 87 days after the initial immunization. The presence of the antibodies in serum of the immunized animals was detected by the Western-blot (FIG. 7). For that purpose, the preparations of the recombinant TROSPA protein were electrophoretically separated and transferred onto a PVDF membrane. The membrane was blocked with 1% BSA solution and, then, incubated with a rabbit serum diluted 10 000 times in a TBSTT buffer. The detection of the bound antibodies was carried out using commercially available anti-rabbit antibodies conjugated with alkaline phosphatase.

B) Immunization of Animals by Oral Administration of the Composition Comprising a Purified Recombinant TROSPA Protein of *Ixodes ricinus* Defined by Sequence SEQ ID No. 3 or Purified Recombinant TROSPA-Salp15 Protein Defined by Sequence SEQ ID No. 4.

An expression of TROSPA genetic construct defined by sequence SEQ ID No. 1 and TROSPA-Salp15 genetic construct defined by sequence SEQ ID No. 2 was performed in a bacterial system, using the Champion™ pET200 Directional TOPO® Expression Kit with BL21 Star™ (DE3) One Shot®, according to the manufacturer's protocol. The recombinant TROSPA protein defined by sequence SEQ ID No. 3 was purified by affinity chromatography with a nickel column. The elution of the protein was carried out at 200 mM concentration of imidazole. The purified preparation of the recombinant TROSPA-Salp15 protein defined by SEQ ID No. 4 was obtained by ion-exchange chromatography, using the DEAE cellulose bed. The elution of the protein was carried out at 200 mM concentration of NaCl. The electrophoretic analysis of the purified recombinant TROSPA protein is presented in FIG. 2B. The electrophoretic analysis of the purified recombinant TROSPA-Salp15 protein in shown in FIG. 4. The protein preparations were dialyzed in a 1× PBS buffer. The 1 mg/ml preparation was used for oral immunization of rats. Using an intragastric probe, the animals were given a composition comprising 200 μg of one of the proteins or a composition comprising 200 μg of one of the proteins and an adjuvant (GEM, 22). The preparations were administered at three time points: on 0, 14, and $28^{th}$ day. The serum was taken after 42 days of initial immunization. The presence of the antibodies in the serum of the immunized animals was detected by ELISA. The ELISA microplate was coated with a recombinant TROSPA protein or recombinant Salp15 protein by incubation of a 5 μg/ml protein solution in a PBSTT buffer. Next, the plate was washed five times with a PBSTT buffer and blocked by incubation in 2% BSA solution in a PBSTT buffer. After the blocking, the plate was washed five times with a PBSTT buffer and incubated by serial dilutions of the sera of the immunized animals or those immunized with an adjuvant only. The detection of the bound antibodies was carried out using commercially available anti-rat secondary antibodies conjugated with alkaline phosphatase, and the product absorbance was measured with Microplate Reader Model 550 by BIORAD. The level of the antibodies was determined using reciprocal serum dilution method (FIGS. 8A and B, 23).

C) Immunization of Animals by Oral Administration of the Composition Comprising Purified TROSPA Proteins of *Ixodes ricinus* Defined by Sequence SEQ ID No. 3, OspA and OspC of *Borrelia burgdorferi* sensu lato.

The expressions of the TROSPA genetic construct defined by sequence SEQ ID No. 1 were carried out in a bacterial system using the Champion™ pET200 Directional TOPO® Expression Kit with BL21 Star™ (DE3) One Shot®, according to the manufacturer's protocol. The recombinant TROSPA proteins defined by sequence SEQ ID No. 3, OspA, and OspC were purified by affinity chromatography with a nickel column. The elution of the proteins was carried out at 200 mM concentration of imidazole. The proteins preparations were dialyzed in a 1× PBS buffer. The 1 mg/ml preparation was used for oral immunization of rats. Using an intragastric probe, the animals were given a composition comprising 200 μg of each protein or a composition of each protein and an adjuvant (GEM, 22). The preparations were given at three time points: on 0, 14, and 28th day. The sera were taken 42 days after the initial immunization. The presence of the antibodies in the sera of the immunized animals was detected using ELISA. The ELISA microplate was coated with the recombinant TROSPA, OspA or OspC protein by incubation of the 5 μg/ml protein solution in a PBSTT buffer. Next, the plate was washed five times with a PBSTT buffer and blocked by incubation in 2% BSA solution in a PBSTT buffer. After the blocking, the plate was washed five times with a PBSTT buffer and incubated with serial dilutions of the sera of the immunized rats or the rats immunized with an adjuvant only. The detection of the bound proteins was carried out using commercially available secondary anti-rat antibodies conjugated with alkaline phosphatase, and the product absorbance was measured using the Microplate Reader Model 550 by BIORAD. The level of the antibodies was determined using reciprocal serum dilution method (FIG. 8C, 23).

The obtained results substantiate the statement that obtained recombinant TROSPA protein defined by sequence SEQ ID No. 3 and TROSPA-Salpl5 protein defined by sequence SEQ ID No. 4 administered into an animal organism via oral or parenteral way are capable of inducing immunological response. Furthermore, the proteins maintain their native structure, which is confirmed by the analysis of the interaction between a recombinant TROSPA protein defined by sequence SEQ ID No. 3 with an OspA proteins from three different *Borrelia* species (i.e. *B. garinii, B. afzelii* and *B. burgdorferi* sensu stricto), presented herein. The antibodies produced in an animal organism after immunization with a recombinant TROSPA protein defined by sequence SEQ ID No. 3 disturb the TROSPA-OspA interaction. Moreover, the antibodies in blood of an immunized vertebrate directed against SalplS antigen present in a recombinant TROSPA-Salp15 protein defined by sequence SEQ ID No. 4 protect an animal against infection on the spirochetes diffusion by destroying the protective coating on the bacteria surface formed by the Salp15—OspC interaction. The observations indicate that the recombinant TROSPA proteins defined by sequence SEQ ID No. 3 and recombinant TROSPA-Salp 15 proteins defined by sequence SEQ ID No. 4 may be the components of Lyme disease vaccine to protect animals against infection with *Borrelia burgdorferi* and minimize the chance of infecting new ticks with *Borrelia burgdorferi*, which, consequently, reduces the pool of spirochetes present in the environment.

LITERATURE

1. Chmielewska-Badera J. 1998. Seroepidemioligic study of Lyme boreliosis in the Lublin Region. *Ann. Agric. Environ. Med.* 5: 183-186.
2. Cisak E., Chmielewska-Badora J., Zwoliński J., Wójcik-Fatla A., Polak J., Dutkiewicz J. 2005. Risk of tick-borne bacterial dieseases among workers of Rortocze National Park (South-Eastern Poland). *Ann. Agric. Environ. Med.* 12: 127-132.
3. Derdáková M., Lenčáková. 2005. Association of genetic variability within the *Borrelia burgdorferi* sensu lato with the ecology, epidemiology of Lyme borreliosis in Europe. *Ann. Agric. Environ. Med.* 12: 165-172
4. Śpiewak R. 2004. Zawodowe choroby skóry u rolników indywidualnych. *Post Dermatol. Alergol.* 21: 278-285.
5. Wodecka B., Skotarczak B. 2000. Genetyczna zmienność *Borrelia burgdorferi* s. l. U kleszczy *Ixodes ricinus* zebranych w pónocnozachodniej Polsce. *Wiadomości parazytologiczne.* 46: 475-485.
6. Vazquez M., Muehlenbein C., Cartter M., Hayes E. B., Ertel S., Shapiro E. D. 2008. Effectiveness of personal protective measures to prevent Lyme disease. *Emerg. Infect. Dis.* 14: 210-216.
7. Connally N. P., Durante A. J., Yousey-Hindes K. M., Meek J. I., Nelson R. S., Heimer R. 2009. Peridomestic Lyme disease prevention: results of a population-based case-control study. *Am. J. Prey. Med.* 37: 201-216.
8. Corapi K. M., White M. I., Phillips C. B., Daltroy L. H., Shadick N. A., Liang M. H. 2007. Strategies for primary and secondary prevention of Lyme disease. *Nat. Clin. Pract. Rheumatol.* 3: 20-25.
9. Steere A. C. 2008. Lyme disease vaccines. In Plotkin S. A., Orenstein W. A., Offit P. A. eds. *Vaccines*. Philadelphia: Saunders-Elsevier, 1253-66.

10. Sigal L. H., Zahradnik J. M., Lavin P., et al. 1998. A vaccine consisting of recombinant *Borrelia burgdorferi* outer-surface protein A to prevent Lyme disease. Recombinant Outer-Surface Protein A Lyme Disease Vaccine Study Consortium. *N. Engl. J. Med.* 339: 216-22.
11. Abbott A. 2006. Lyme disease: uphill struggle. Nature 439,524-525.
12. Croke C. L., Munson E. L., Lovrich S. D., et al. 2000. Occurrence of severe destructive Lyme arthritis in hamsters vaccinated with outer surface protein A and challenged with *Borrelia burgdorferi. Infect. Immun.*68: 658-63.
13. Nardelli D. T., Munson E. L., Callister S. M., Schell R. F. 2009. Human Lyme disease vaccines: past and future concerns. *Future Microbiol* 4: 457-69.
14. Drouin E. E, Glickstein L., Kwok W. W., Nepom G. T., Steere A. C. 2008. Human homologues of a *Borrelia* T cell epitope associated with antibioticrefractory Lyme arthritis. *Mol. Immunol.* 45: 180-9.
15. Earnhart, C. G., Buckles, E. L., and. Marconi, R. T. 2007. Development of an OspC-based tetravalent, recombinant, chimeric vaccinogen that elicits bactericidal antibody against diverse Lyme disease spirochete strains. *Vaccine* 25: 466-480.
16. Bhattacharyaa D., Bensacib M., Lukerc K. E., et. al. 2011. Development of a baited oral vaccine for use in reservoir-targeted strategies against Lyme disease. *Vaccine,* 29: 7818- 7825.
18. Dai J., Wang P., Adusumilli S., et. al., 2009. Antibodies against a Tick Protein, Salp15, Protect Mice from the Lyme Disease Agent. *Cell Host & Microbe,* 6: 482-492.
19. Pal U., Li X., Wang T., Montgomery R. R. et al. 2004. TROSPA, an Ixodes scapularis receptor for *Borrelia burgdorferi. Cell,* 119: 457-468.
20. Hovius J. W., Ramamoorthi N., Van't Veer C. et al. 2007. Identification of Salp15 homologues in *Ixodes ricinus* ticks. *Vector Borne Zoonotic Dis.* 7: 296-303.
21. Dai J., Wang P., Adusumilli S., et. al., 2009. Antibodies against a Tick Protein, Salp15, Protect Mice from the Lyme Disease Agent. *Cell Host & Microbe,* 6: 482-492.
22. Saluja V., Visser M. R., van. Roosmalen M. L. et al. 2010. Gastro-intestinal delivery of influenza subunit vaccine formulation adjuvanted with Gram-positive enhancer matrix (GEM) particles. Eur. J. *Pharm. Biopharm.* 76: 470-474.
23. Frey A., Di Canzio J. i Zurakowski D. 1998. A statistically defined endpoint titer determination method for immunoassays. *J. Immunol. Meth.* 221:35-41

The invention claimed is:

1. An immunogenic composition comprising a recombinant TROSPA protein defined by SEQ ID NO: 3 or a recombinant TROSPA-Salp15 protein defined by SEQ ID NO: 4, wherein the immunogenic composition is administered orally.

2. A method for producing the immunogenic composition of claim 1, comprising the steps of: expression of a genetic construct defined by SEQ ID NO: 1 or SEQ ID NO: 2 in *E. coli*, isolation and purification of the expressed protein defined by SEQ ID NO: 3 or SEQ ID No: 4, respectively and preparing an immunogenic composition of said protein in a pharmaceutically acceptable buffer.

3. The immunogenic composition of claim 1 further comprising a pharmaceutically acceptable diluent and optionally an adjuvant, carrier and/or vehicle.

4. A kit comprising the immunogenic composition of claim 1.

5. A kit comprising the immunogenic composition of claim 3.

* * * * *

SEQUENCE LISTING

```
<160> NUMBER OF SEQ ID NOS: 15

<210> SEQ ID NO 1
<211> LENGTH: 606
<212> TYPE: DNA
<213> ORGANISM: Artificial Sequence
<220> FEATURE:
<221> NAME/KEY: source
<222> LOCATION: 1..606
<223> OTHER INFORMATION: /mol_type="other DNA"
      /note="sequence of TROSPA genetic construct"
      /organism="Artificial Sequence"

<400> SEQUENCE: 1

atgcggggtt ctcatcatca tcatcatcat ggtatggcta gcatgactgg tggacagcaa      60

atgggtcggg atctgtacga cgatgacgat aaggatcatc ccttcaccat ggcggctatg     120

gaggctatgg cggtggatat ggaggctatg gcggcggcta tggcggcggc tatggtggct     180

acggacacgg tggcttcctc ggcggcttcg gctatggcca cggaggctac ggtggctatg     240

gacacggcgt cgctgtcgct gccgctccag ttgtcgccaa ggtcgctgcc ccagtcgtcg     300

ctgtcggcca cggcggccac ggtggctacg gacacggtgg tttcctcggc ggatacggag     360

gttacggaca cggaggattc ggcggctacg gtctcggcca cggcgtcgct gtccatgctg     420

ccccagttgt cgccaaggtc gctgccccag tcgtcgctgt cggccacggc tacggaggct     480

tcggttacag cggatatggc ggacacggct acggacacta agcaattcat ctcaaaggga     540

aaccaacact tcttcgccgc ttcttattta tgcgcttggg ccgaccagag cgccgctgga     600

agttga                                                                606

<210> SEQ ID NO 2
<211> LENGTH: 1104
<212> TYPE: DNA
<213> ORGANISM: Artificial Sequence
<220> FEATURE:
<221> NAME/KEY: source
<222> LOCATION: 1..1104
<223> OTHER INFORMATION: /mol_type="other DNA"
      /note="sequence of TROSPA-Salp15 genetic construct "
```

-continued

/organism="Artificial Sequence"

<400> SEQUENCE: 2

```
atgcggggtt ctcatcatca tcatcatcat ggtatggcta gcatgactgg tggacagcaa     60
atgggtcggg atctgtacga cgatgacgat aaggatcatc ccttcaccat ggcggctatg    120
gaggctatgg cggtggatat ggaggctatg gcggcggcta tggcggcggc tatggtggct    180
acggacacgg tggcttcctc ggcggcttcg gctatggcca cggaggctac ggtggctatg    240
gacacggcgt cgctgtcgct gccgctccag ttgtcgccaa ggtcgctgcc ccagtcgtcg    300
ctgtcggcca cggcggctac ggtggctacg gacacggtgg tttcctcggc ggatacggag    360
gttacggaca cggaggattc ggcggctacg gtctcggcca cggcgtcgct gtccatgctg    420
ccccagttgt cgccaaggtc gctgccccag tcgtcgctgt cggccacggc tacggaggct    480
tcggttacgg cggatatggc ggacacggct acggacacta agcaattcat ctcaaaggga    540
aaccaacact tcttcgccgc ttcttattta tgcgcttggg ccgaccagag cgccgctgga    600
agtgaagcgg cggcgaaaga agcggcggcg aaagaagcgg cggcgaaaga agcggcggcg    660
aaagaagcgg cggcgaaaga aaacctgtat tttcagggaa tggaaagctt tgttgccatg    720
aaagttgttt gcattaccgt gctgtttgtt attgttgccg ttaatgaaag cgcaaccagc    780
gaagcacgta ccagcagcgc agcaaaagaa accaaaaaaa aaaatgtgac cctgcatttt    840
ccgagctata tccgtaatcc gcagaaactg gcactggaac tgctggaaat ttgcaaaaat    900
aataaaagcc gcaatagcct gccgagcacc aattatagcg ccattaatga taaatatgtg    960
gattttaaaa attgcacctt tctgtgcaaa catgccgaag atcgtaatgt taccctggat   1020
ctgcctccga ataccctgtg tggtccgaat ggtgaaacct gtgcagaaaa aagcaaatgc   1080
gttggtcata ttccgggttg ttaa                                          1104
```

<210> SEQ ID NO 3
<211> LENGTH: 201
<212> TYPE: PRT
<213> ORGANISM: Artificial Sequence
<220> FEATURE:
<221> NAME/KEY: SOURCE
<222> LOCATION: 1..201
<223> OTHER INFORMATION: /mol_type="protein"
/note="sequence of recombinant TROSPA protein - a product of the TROSPA genetic construct expression"
/organism="Artificial Sequence"

<400> SEQUENCE: 3

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

His Pro Phe Thr Met Ala Ala Met Glu Ala Met Ala Val Asp Met Glu
        35                  40                  45

Ala Met Ala Ala Ala Met Ala Ala Ala Met Val Ala Thr Asp Thr Val
    50                  55                  60

Ala Ser Ser Ala Ala Ser Ala Met Ala Thr Glu Ala Thr Val Ala Met
65                  70                  75                  80

Asp Thr Ala Ser Leu Ser Leu Pro Leu Gln Leu Ser Pro Arg Ser Leu
                85                  90                  95

Pro Gln Ser Ser Leu Ser Ala Thr Ala Ala Thr Val Ala Thr Asp Thr
            100                 105                 110

Val Val Ser Ser Ala Asp Thr Glu Val Thr Asp Thr Glu Asp Ser Ala
```

-continued

```
        115                 120                 125

Ala Thr Val Ser Ala Thr Ala Ser Leu Ser Met Leu Pro Gln Leu Ser
    130                 135                 140

Pro Arg Ser Leu Pro Gln Ser Ser Leu Ser Ala Thr Ala Thr Glu Ala
145                 150                 155                 160

Ser Val Thr Ala Asp Met Ala Asp Thr Ala Thr Asp Thr Lys Gln Phe
                165                 170                 175

Ile Ser Lys Gly Asn Gln His Phe Phe Ala Ala Ser Tyr Leu Cys Ala
            180                 185                 190

Trp Ala Asp Gln Ser Ala Ala Gly Ser
        195                 200


<210> SEQ ID NO 4
<211> LENGTH: 367
<212> TYPE: PRT
<213> ORGANISM: Artificial Sequence
<220> FEATURE:
<221> NAME/KEY: SOURCE
<222> LOCATION: 1..367
<223> OTHER INFORMATION: /mol_type="protein"
      /note="The sequence of recombinant TROSPA-Salp15 protein - a prod
      uct of the TROSPA-Salp15 genetic product expression"
      /organism="Artificial Sequence"

<400> SEQUENCE: 4

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

His Pro Phe Thr Met Ala Ala Met Glu Ala Met Ala Val Asp Met Glu
        35                  40                  45

Ala Met Ala Ala Ala Met Ala Ala Ala Met Val Ala Thr Asp Thr Val
    50                  55                  60

Ala Ser Ser Ala Ala Ser Ala Met Ala Thr Glu Ala Thr Val Ala Met
65                  70                  75                  80

Asp Thr Ala Ser Leu Ser Leu Pro Leu Gln Leu Ser Pro Arg Ser Leu
                85                  90                  95

Pro Gln Ser Ser Leu Ser Ala Thr Ala Ala Thr Val Ala Thr Asp Thr
            100                 105                 110

Val Val Ser Ser Ala Asp Thr Glu Val Thr Asp Thr Glu Asp Ser Ala
        115                 120                 125

Ala Thr Val Ser Ala Thr Ala Ser Leu Ser Met Leu Pro Gln Leu Ser
    130                 135                 140

Pro Arg Ser Leu Pro Gln Ser Ser Leu Ser Ala Thr Ala Thr Glu Ala
145                 150                 155                 160

Ser Val Thr Ala Asp Met Ala Asp Thr Ala Thr Asp Thr Lys Gln Phe
                165                 170                 175

Ile Ser Lys Gly Asn Gln His Phe Phe Ala Ala Ser Tyr Leu Cys Ala
            180                 185                 190

Trp Ala Asp Gln Ser Ala Ala Gly Ser Glu Ala Ala Ala Lys Glu Ala
        195                 200                 205

Ala Ala Lys Glu Ala Ala Ala Lys Glu Ala Ala Ala Lys Glu Ala Ala
    210                 215                 220

Ala Lys Glu Asn Leu Tyr Phe Gln Gly Met Glu Ser Phe Val Ala Met
225                 230                 235                 240

Lys Val Val Cys Ile Thr Val Leu Phe Val Ile Val Ala Val Asn Glu
                245                 250                 255
```

-continued

Ser Ala Thr Ser Glu Ala Arg Thr Ser Ser Ala Ala Lys Glu Thr Lys
260 265 270

Lys Lys Asn Val Thr Leu His Phe Pro Ser Tyr Ile Arg Asn Pro Gln
275 280 285

Lys Leu Ala Leu Glu Leu Leu Glu Ile Cys Lys Asn Asn Lys Ser Arg
290 295 300

Asn Ser Leu Pro Ser Thr Asn Tyr Ser Ala Ile Asn Asp Lys Tyr Val
305 310 315 320

Asp Phe Lys Asn Cys Thr Phe Leu Cys Lys His Ala Glu Asp Arg Asn
325 330 335

Val Thr Leu Asp Leu Pro Pro Asn Thr Leu Cys Gly Pro Asn Gly Glu
340 345 350

Thr Cys Ala Glu Lys Ser Lys Cys Val Gly His Ile Pro Gly Cys
355 360 365

<210> SEQ ID NO 5
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
/note="DNA TROSPAF oligonucleotides"
/organism="Artificial Sequence"

<400> SEQUENCE: 5
tttggtctca aggtatggcg gctatggagg c 31

<210> SEQ ID NO 6
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="DNA"
/note="DNA TROSPAR oligonucleotides"
/organism="Artificial Sequence"

<400> SEQUENCE: 6
atatttaaat tcaacttcca gcggcgc 27

<210> SEQ ID NO 7
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="DNA"
/note="DNA TROTOPF oligonucleotides"
/organism="Artificial Sequence"

<400> SEQUENCE: 7
caccatggcg gctatggagg c 21

<210> SEQ ID NO 8
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="DNA"

/note="DNA TRORPST oligonucleotide"
/organism="Artificial Sequence"

<400> SEQUENCE: 8
atctgcagtc aacttccagc ggcgctctgg tcgg 34

<210> SEQ ID NO 9
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="DNA"
/note="DNA FUS11Af oligonucleotide"
/organism="Artificial Sequence"

<400> SEQUENCE: 9
caccatggcg gctatggagg ctatggcgg 29

<210> SEQ ID NO 10
<211> LENGTH: 30
<212> TYPE: DNA
<213> ORGANISM: Artificial Sequence
<220> FEATURE:
<221> NAME/KEY: source
<222> LOCATION: 1..30
<223> OTHER INFORMATION: /mol_type="DNA"
/note="DNA FUS11Ar oligonucleotide"
/organism="Artificial Sequence"

<400> SEQUENCE: 10
atggatcctt aacaacccgg aatatgacca 30

<210> SEQ ID NO 11
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="DNA"
/note="OspAf - Nucleotide sequences of the PCR reaction starters"
/organism="Artificial Sequence"

<400> SEQUENCE: 11
caccatgaaa aaatatttat tgggaatagg t 31

<210> SEQ ID NO 12
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="DNA"
/note="OspAr - Nucleotide sequences of the PCR reaction starters"
/organism="Artificial Sequence"

<400> SEQUENCE: 12
ccttatttta aagcgttttt a 21

<210> SEQ ID NO 13
<211> LENGTH: 27
<212> TYPE: DNA
<213> ORGANISM: Artificial Sequence
<220> FEATURE:
<221> NAME/KEY: source
<222> LOCATION: 1..27

-continued

```
<223> OTHER INFORMATION: /mol_type="DNA"
      /note="OspCf - Nucleotide sequences of the PCR reaction starters"
      /organism="Artificial Sequence"

<400> SEQUENCE: 13

caccatgaaa aagaatacat taagtgc                                       27


<210> SEQ ID NO 14
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="DNA"
      /note="OspCr - Nucleotide sequences of the PCR reaction starters"
      /organism="Artificial Sequence"

<400> SEQUENCE: 14

ttaaggtttt ttttggactt tctgc                                         25


<210> SEQ ID NO 15
<211> LENGTH: 370
<212> TYPE: DNA
<213> ORGANISM: Artificial Sequence
<220> FEATURE:
<221> NAME/KEY: source
<222> LOCATION: 1..370
<223> OTHER INFORMATION: /mol_type="DNA"
      /note="Sequence from fig. 9"
      /organism="Artificial Sequence"

<400> SEQUENCE: 15

ataggcgcca gcaaccgcac ctgtggcgcc ggtgatgccg gccacgatgc gtccggcgta    60

gaggatcgag atctcgatcc cgcgaaatta atacgactca ctatagggga attgtgagcg   120

gataacaatt cccctctaga aataattttg tttaacttta agaaggagat atacatatgc   180

ggggttctca tcatcatcat catcatggta tggctagcat gactggtgga cagcaaatgg   240

gtcgggatct gtacgacgat gacgataagg atcatccctt caccaagggc gagctcaacg   300

atccggctgc taacaaagcc cgaaaggaag ctgagttggc tgctgccacc gctgagcaat   360

aactagcata                                                          370
```